US007207333B2

(12) United States Patent
Tohara

(10) Patent No.: US 7,207,333 B2
(45) Date of Patent: Apr. 24, 2007

(54) NOSE MASK

(75) Inventor: Hirotaka Tohara, Ehime (JP)

(73) Assignee: Bio International Co., Ltd., Ehime (JP)

( * ) Notice: Subject to any disclaimer, the term of this patent is extended or adjusted under 35 U.S.C. 154(b) by 20 days.

(21) Appl. No.: 10/514,431

(22) PCT Filed: May 21, 2003

(86) PCT No.: PCT/JP03/06307

§ 371 (c)(1),
(2), (4) Date: Nov. 16, 2004

(87) PCT Pub. No.: WO03/097168

PCT Pub. Date: Nov. 27, 2003

(65) Prior Publication Data

US 2005/0121036 A1 Jun. 9, 2005

(30) Foreign Application Priority Data

May 22, 2002 (JP) ............................ 2002-148316
Aug. 7, 2002 (JP) ............................ 2002-230316

(51) Int. Cl.
*A61M 16/00* (2006.01)
*A61M 15/00* (2006.01)

(52) U.S. Cl. ............................ 128/206.11; 128/207.18

(58) Field of Classification Search ........... 128/207.18, 128/206.11, 205.27, 200.26, 205.29
See application file for complete search history.

(56) References Cited

U.S. PATENT DOCUMENTS 1,322,375 A * 11/1919 Un ........................ 128/206.11
2,237,954 A * 4/1941 Wilson .................. 128/204.12
3,747,597 A * 7/1973 Olivera ................. 128/206.11
4,221,217 A 9/1980 Amezcua
4,327,719 A * 5/1982 Childers ............... 128/206.11
5,417,205 A * 5/1995 Wang ..................... 128/206.11
5,568,808 A * 10/1996 Rimkus ................. 128/206.11
6,484,725 B1 * 11/2002 Chi ............................ 128/858
2004/0089303 A1 * 5/2004 Chien .................... 128/206.11

FOREIGN PATENT DOCUMENTS

| | | | |
|---|---|---|---|
| FR | 2417304 | * | 9/1979 |
| FR | 2504003 | * | 10/1982 |
| JP | 61-39556 | * | 3/1986 |
| JP | 2-126668 | | 10/1990 |
| JP | 3-57511 | | 6/1991 |
| JP | 3-52457 | | 7/1998 |

* cited by examiner

*Primary Examiner*—Teena Mitchell
(74) *Attorney, Agent, or Firm*—Wenderoth, Lind & Ponack, L.L.P.

(57) ABSTRACT

A nose mask having either one of several types of mask parts with different functions selectively fitted to an installation shaft, usable without impairing the attractiveness of a nose, and formed so that, when the installation shaft is inserted from nostrils into nose vestibules a nasal septum is held so as to install the mask part. The mask part is engaged with the tips of the installation shaft by caps and stoppers, and cellulose sponges and filters are arranged alternately with each other. The mask parts can be classified into a plurality of groups according to functions, i.e those for underwater action without gas permeability and water permeability, those having fine-mesh filters formed of fiber material with gas permeability and excellent hygroscopicity and capable of filtering contaminated air, and those allowing liquid such as chemicals to be impregnated therein.

7 Claims, 4 Drawing Sheets

NOSE MASK

BACKGROUND OF THE INVENTION

1. Technical Field

A nose mask according to this invention relates to a nose mask whose user inserts a mask portion of an arrangement axle from nares into a nasal vestibule (vestibulum nasi), so that a nasal septum is sandwiched by the arrangement axle, whereby the mask portion is fitted in a nasal cavity. The invention is for providing a nose mask, applicable for various purposes including a filtering mask preventing the user from inhaling pollen, dust etc., a mask for a treatment tool by absorbing and evaporating a nose drug impregnated in a hygroscopic mask portion, and a nose stopper for swimming performance.

2. Description of Related Art

In conjunction with a mask fitted in the nares when it is in use, Japanese Patent Laid-open Nos. 8-71170, 9-294819, and 11-137702 are issued. Each of the masks published in these official gazettes is for inserting a filter into an entrance of nares or for covering the nares with the filter. These filters are filtering materials for passing through and purifying the air. As an arrangement tool for inserting the filter into the nares is engaged in the entrance of the nares or a head of the nose in each of the conventional nose masks, and the nose swells due to the filter being inserted into the nares. As the head of the nose is covered by an arrangement portion for arranging the filter to cover the nares, an appearance of the nose is further spoiled from an aesthetic point of view.

However, such a prior-art nose mask is originally for not only absorbing the polluted air, but also filtering the polluted air. The nose mask can be used in such a multi-functional way as a nose treatment tool for pollinosis etc. or as a nose stopper for the swimming performance. Floating dust in the air has various kinds of pollen, polluted dust, malodor etc. The prior-art nose mask is engaged in the nares for preventing the user from inhaling dust, and the mask portion must be fixed in the arrangement tool. To achieve this, the nose mask has been limited to only one kind. As a result, the prior-art nose mask cannot select the multi-functional nose mask respectively corresponding to floating dust, medical treatment, and swimming. Furthermore, there was a disadvantage on the mask fitted in a position near the outside of holes of the nose, which is that the mask is easily released and even if the mask fits the nose, the mask spoils the appearance of the face as respective holes of the nose are widened.

SUMMARY OF THE INVENTION

This invention is proposed as a new nose mask in which several kinds of mask portions, each of which has a distinctive function, are selectively fitted on tips of an arrangement axle.

The nose mask, is engaged within the nares without spoiling the appearance of the nose even if the masks are engaged with a nasal cavity. The masks are separately manufactured in terms of their functions, such as a function to treat the nose by preventing the user from inhaling pollen, malodor, dust etc. or a function to prevent an invasion of water through swimming performance. This invention intends to provide a nose mask wearable in the nares by means of selecting either a mask portion or a mask stopper.

In order to solve the above-mentioned problems, a nose mask of the present invention comprises an arrangement axle and a mask portion coupled with a tip of the arrangement axle. The mask portion with a distinctive function is arranged on the arrangement axle, and the arrangement axle is inserted from the nares into a nasal vestibule, so that a nasal septum is sandwiched by the arrangement axle in front of a nasal cavity. The tip of the arrangement axle is coupled with the mask portion by means of a cap and a stopper. The mask portion comprises a material selected from the group comprising a fiber with air permeability and hygroscopicity, and a rubber without liquid permeability.

Some of the materials have a minute mesh capable of filtrating the polluted air for impregnating infiltrative liquid. The materials of the mask portion include fiber, which is used for a medical treatment as preventing from inhaling the polluted air without spoiling the appearance of the nose, and a rubber having no water permeability for swimming.

The tip of the arrangement axle wearable in the nose by being inserted from the nares is provided with the arrangement portion consisting of the cap and the stopper, so that a cellulose sponge and filters can be alternately arranged. The cellulose sponge has a flat surface with a hole for engaging, a tip of the cap being inserted in the hole. Then, the filters also has a hole for engaging, the tip of the cap being inserted in the hole. The cellulose sponge and the filters can be alternately arranged and fixed by means of the stopper on the tip of the cap; the cap is arranged on the tip of the arrangement axle.

The arrangement axle is made of either synthetic resin or vegetable resin with a moderate elasticity. The mask portion fitted on the tip of the arrangement axle is made of a material with air permeability and hygroscopicity such as fiber and sponge. The material is sometimes made of either a soft synthetic resin or rubber, which can prevent from an invasion of water. The function of the mask portion is different according to its material, and the kind of the mask is increased according to its aim. The mask portion fundamentally has a structure in which a cellulose sponge and filter layers comprising a minute mesh are alternately arranged and fitted by the cap and the stopper. Instead of the above-identified mask portion, the stopper made of silicone rubber may be used.

According to an aspect of this invention, there is provided with a nose mask characterized in that the arrangement axle is inserted from the nares into the nasal vestibule and that a plurality of mask portions are fitted on the tips of the arrangement axle which is to fit the mask portions to the nasal cavity. The mask portion has the sponge and the filter layers both fitted on the tip of the arrangement axle by the cap and the stopper, so as to be applicable for filtering polluted materials such as pollen, dust, malodor in the air and for treating a nose etc. Instead of said mask portion, a rubber stopper portion can be fixed on the tip of the arrangement axle selectively coupled with the cap and the stopper.

According to another aspect of this invention, there is provided with a structure in which a cellulose sponge and filters are alternately arranged on the mask portion and the mask portion is fitted on the tip of the arrangement axle. In this case, the cellulose sponge and the filter are alternately inserted in an axle with an axle hole in the center of the cap, with the stopper inserted into said axle. As the axle tip and the stopper are coupled and formed in the claw-shaped configuration, the cellulose sponge and the filter are fixed onto the axle of the cap. This invention is characterized in that as the tip of the arrangement axle is formed in the claw-shaped, the tip is coupled with a coupling portion fitted on the cap and the mask portion is fitted onto the arrangement axle. There is thus an advantage in preventing the mask portion of the engagement axle from being released because of the claw-shaped configuration.

According to still another aspect of this invention, the stopper is inserted into said axle and the axle tip and the stopper are coupled and formed in the claw-shaped configuration, thereby the cellulose sponge and the filter are fixed to the axle of the cap. The present invention is characterized in that the tip of the arrangement axle is formed in the claw-shaped, the tip is coupled with the coupling portion fitted on the cap and the mask portion is fitted onto the arrangement axle. There is thus an advantage in preventing the mask portion of the engagement axle from being released because of the claw-shaped configuration.

According to yet another aspect of this invention, the mask portion is fitted on the tip of the arrangement axle, which is inserted from the nares to a nasal septum and fitted on the very inner part of a nasal cavity, where one mask portion selected from several mask portions can be fitted. For example, a nose stopper can be fitted on the tip of the arrangement axle instead of a nose mask. There are other masks which can be selectively used including; a nose mask for filtrating polluted substances such as pollen, dust, malodor etc. floating in the air; a nose mask for treating a nose; a nose stopper for the swimming performance; and a nose stopper made of silicone rubber.

According to further aspect of this invention, a nose stopper is provided on the tip of said arrangement axle. The feature is that the arrangement axle is inserted from the nares into the nasal vestibule so that the nasal septum is sandwiched by the arrangement axle, whereby it prevents from causing stimulus by the invasion of water.

DETAILED DESCRIPTION OF THE INVENTION

The technical idea of the present invention is embodied in the embodiment described below.

Figure 1:
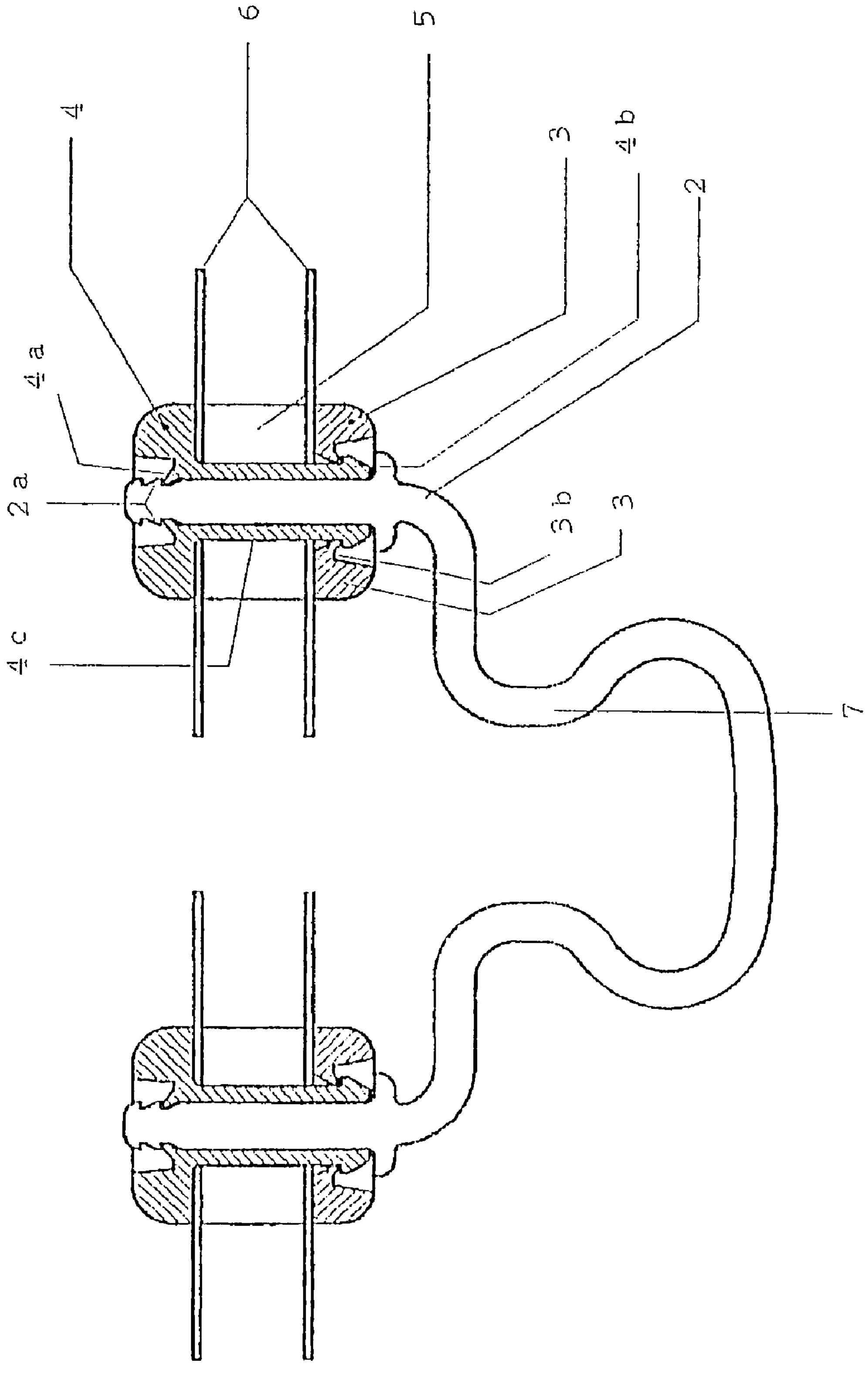
FIG. 1 is a sectional view showing a front of the nose mask.
Figure 2:
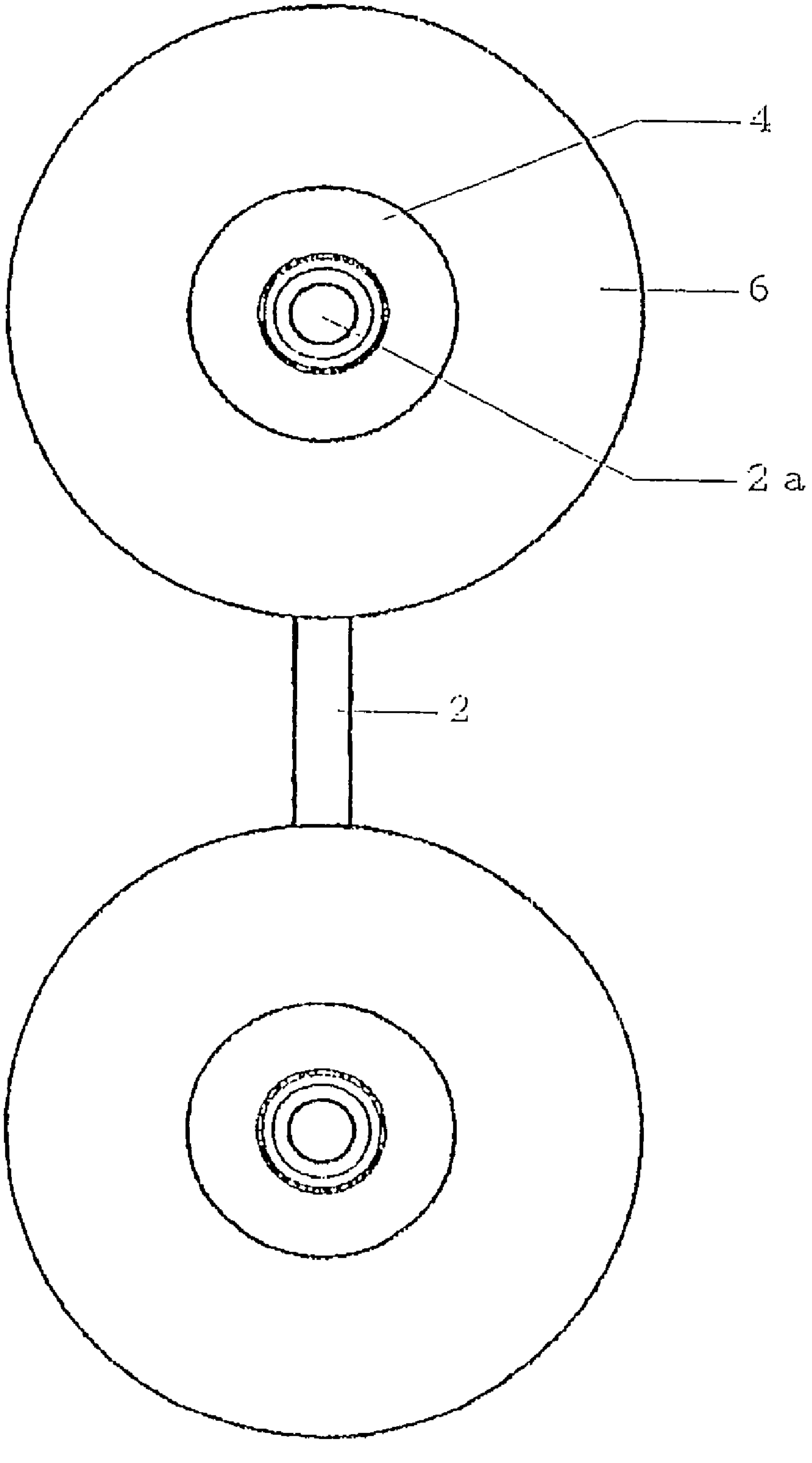
FIG. 2 is a plan view of the mask portion.
Figure 3:
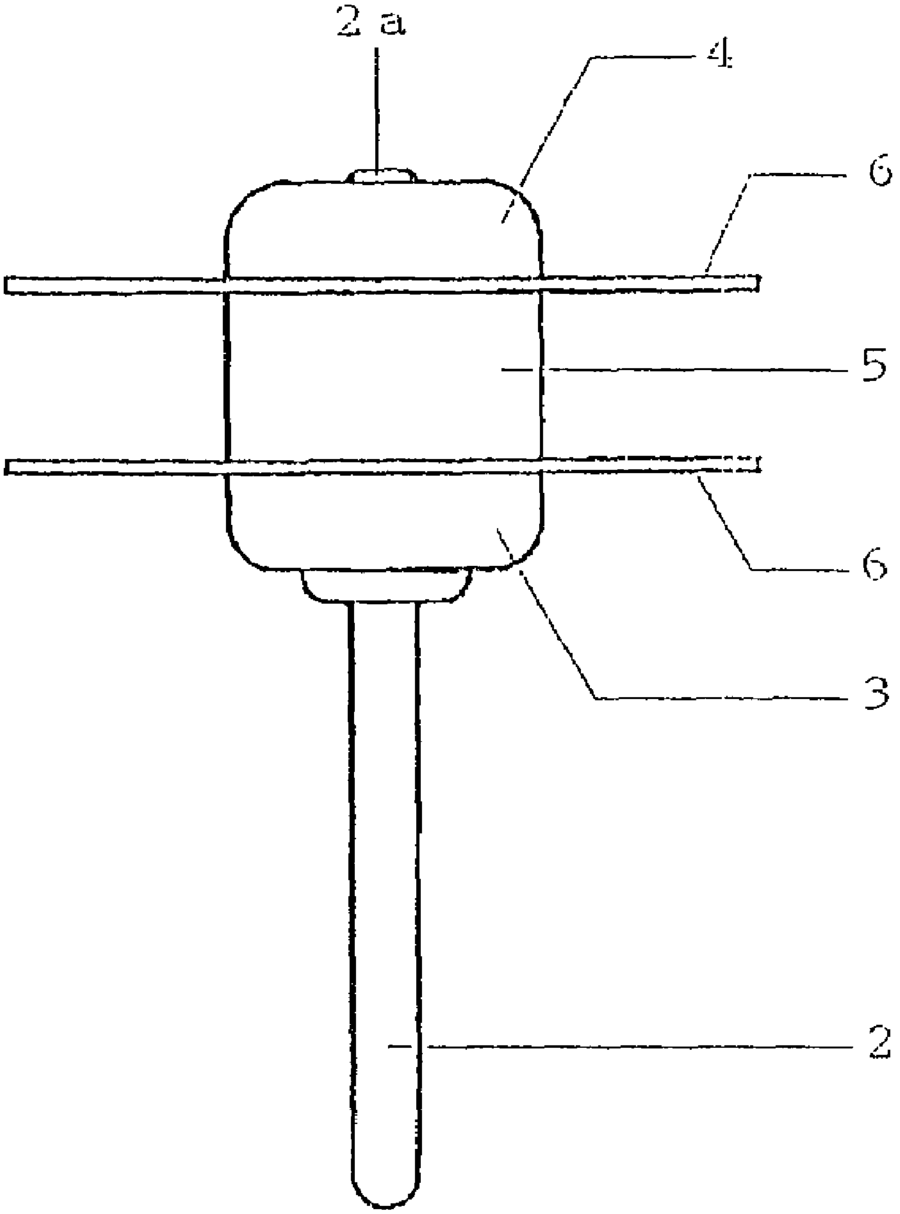
FIG. 3 is a side view of the nose mask.

Referring to FIG. 1, in a nose mask, to fit each mask portion on an arrangement portion of each tip of an arrangement axle (2). An axle (4*c*) is provided on a cap (4) with an axle hole in the center of the cap (4), and a claw (4*b*), provided on a tip of the axle, is engaged with a claw (3*b*) provided on a stopper (3). A claw (4*a*), provided on a center part of the cap, is engaged with a claw (2*a*) of the tip of the arrangement axle (2), and the mask portion, comprising a cellulose sponge (5) and filters (6), is fitted on the arrangement portion of the arrangement axle (2). As the cap (4) is engaged with the stopper (3) by their claws as well as the cap (4) and the arrangement axle (2), the cellulose sponge (5) and the filters (6) are configured so as not to be released from the arrangement axle (2), which has the mask portions.

Figure 4:
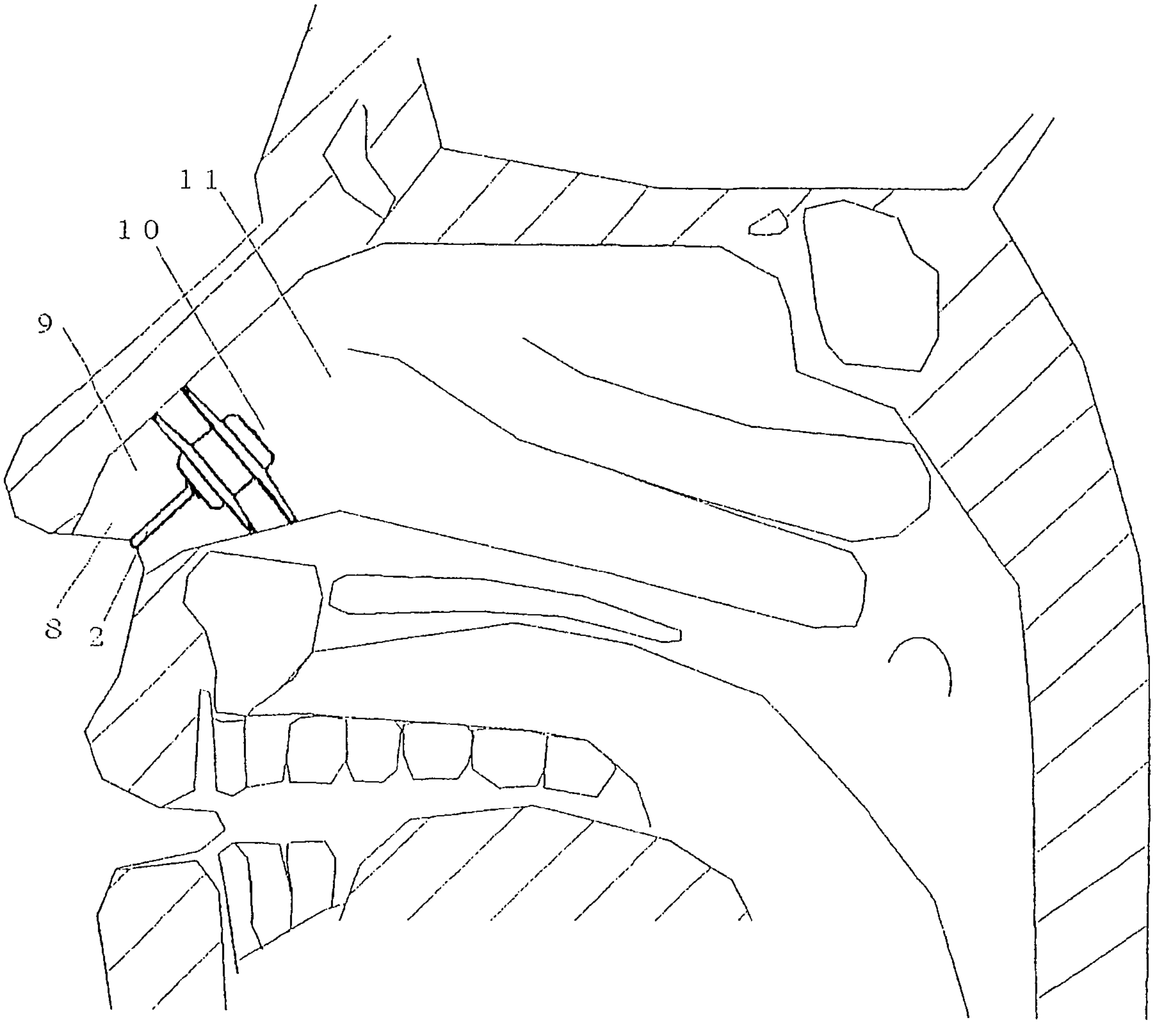
FIG. 4 is a sectional view depicting conditions of use of the nose mask from a side surface of a user's face.

Braces (7) are formed on the arrangement axle (2). Referring to FIG. 4, the arrangement axle sandwiches a nasal septum (9) so that the mask portions are fitted in a nasal vestibule (10). The arrangement axle, when inserted into the nasal vestibule, sandwiches the nasal septum (9) between the braces (7) without spoiling an appearance of nares, so that the mask portions are stabilized and the nose mask is not released and dropped due to internal pressure caused by sneezing. For the purpose of preventing an internal surface of a nasal cavity (11) from being subjected to excessive stimulus, the materials of the cellulose sponge and the filters have flexibility. The arrangement axle is made of synthetic resin or vegetable resin with elasticity, and is provided with the braces (7), which are inserted from the nares to sandwich the nasal septum by using their own shape to prevent the nose mask from being easily dropped.

The mask portions, which are to be fitted on the tips of the arrangement axle, are not positioned in the very inner part of the nasal cavity. A nose stopper for the swimming performance, filter layers for filtering and purifying the air polluted by dust, pollen etc., and a cellulose sponge capable of infiltrating drug for a medical treatment are produced, and at least any two of the three can be fitted on the arrangement axle (2) by engaging the cap (4) with the stopper (3).

Preferably, the mask portions have, as well as the cellulose sponge does, air permeability and hygroscopicity so as not to over-stimulate an internal mucous membrane, and flexibility to properly fit an internal shape of the nasal cavity. An elastic body for the nose stopper to be fitted on the arrangement axle is represented by a rubber plate, which does not infiltrate water for the swimming performance. A rubber plate made of silicone rubber is preferable. For filtering the polluted air including malodor such as pollen, dust, smoke, and other rotten smells, and poisonous materials such as nitrogen oxide and dioxin, the filters preferably have a minute mesh capable of purifying the air, and is made of a minute fiber represented by paper, cotton, synthetic resin and vegetable resin, and capable of filtering the above-mentioned polluted air. Furthermore, there is a cellulose sponge, which has hygroscopicity and liquid permeability for absorbing and impregnating drugs with an elastic body when the drug is dropped. Any of the above-described features is necessarily fitted on the arrangement axle.

The arrangement axle (2) is to be inserted not more than 15 mm from a naris (8) to sandwich and fix the nasal septum. Therefore, it is important to keep the length of the arrangement axle less than 15 mm to avoid stimulating the nasal cavity (11). This supports the mask portions not to be inserted to the very inner part of the nasal cavity. It is preferable that the mask portions are flexible elastic bodies hygroscopic for not stimulating the internal mucous membrane of a nose, and capable of keeping moist with dropped drug and air permeability. Instead of the mask portions, a rubber plate made of a material with no liquid permeability is sometimes fitted on the tip of the arrangement axle (2) by the cap and the stopper.

The mask portion is sometimes used as a treatment tool by which when liquid drug is applied on the mask portion the liquid is impregnated with the elastic body, by fitted on the nose, to absorb the drug which is evaporated into the nasal cavity by body temperature and breath. In an embodiment, the elastic body of the mask portion is used as a filter for filtering polluted air, while in another embodiment, the elastic body is used for medical treatment. An elastic body, without liquid permeability, can be fitted on the arrangement axle in accordance with its function to prevent water from entering the nasal cavity.

An embodiment will be described in detail with reference to the drawings.

The embodiment represents an example of the present invention on the premise of enabling the user to selectively fit plural mask portions having distinctive functions on the arrangement axle, and also to carry the nose mask with them.

As a preferred embodiment, the nose mask of the present invention is characterized in that tips of a 15 mm arrangement axle are inserted in nares (8) so as to sandwich a nasal septum (9) by the use of braces (7), and that the arrangement axle is carefully inserted in a nasal vestibule (10) so that the mask portions fitted on the tips of the arrangement axle are not inserted into the very inner part of a nasal cavity.

A claw (2*a*) is provided on the tip of the arrangement axle (2), and the tip of the arrangement axle (2) is inserted into an axle hole provided in the center of a cap (4). The claw (2*a*) is coupled with a claw (4*a*) and is formed in the claw-shape for securing the coupling. A claw (4*b*) is provided on a tip of a lower part of the cap (4) and coupled with a claw (3*b*) of a stopper (3) so as to fix the mask portion on the tip of the arrangement axle (2). A cellulose sponge (5) and filters (6) are alternately arranged on this mask portion in accordance with combination of several functions.

In a case where a nose mask is used as a nose stopper for swimming purposes, a rubber plate with no liquid permeability, such as flexible rubber, is fitted on the tip of the arrangement axle (2) by means of the cap (4) and the stopper (3). In a case where the nose mask is used as a filtering mask for polluted air, it is preferable that filter layers and a cellulose sponge which are made of a minute mesh with air permeability and hygroscopicity are alternately arranged to filter and purify the polluted air absorbed from the nares. Furthermore, in a case where the nose mask is used for medical treatment, a mask portion, which is made of fiber and has good liquid drug permeability, is fitted on the tip of the arrangement axle (2). This nose mask for the medical treatment is characterized in that when liquid drug is applied on the mask portion, the drug is filtrated and impregnated.

The above-mentioned arrangement axle (2) is inserted from the nares, kept in position by the braces (7), and thereby is kept substantially invisible from outside. Therefore, people around the nose-mask user will not notice the use of the nose mask. The arrangement axle (2), which is made of either flexible synthetic resin or vegetable resin, is inserted into a nasal vestibule (10), which, for example, is preferably positioned about 15 mm from the nares. Although the length of the arrangement axle to be inserted into the nares (8) varies from less to more than 15 mm, the length of the arrangement axle to be inserted into the nose must be adjusted in order to avoid causing excess stimulus.

INDUSTRIAL APPLICABILITY

An actual use of the embodiment will be explained below. The nose mask is characterized in that distinctive mask portions can be fitted on the arrangement axle (2) according to a functionally different uses including swimming, anti-pollinosis, and medical treatment such as stoppage of nose bleeding. For example, the nose mask to be used in a place where there is a lot of pollen and dust is configured so that a mask portion of filter layers, which is suitable for purifying the air, is fitted on the tip of the arrangement axle (2). In the case of the nose stopper for swimming, a rubber plate is fitted for a mask portion instead of the filters. In the case of the treatment nose mask for nose bleeding, a cellulose sponge on which a liquid drug is provided is used as the mask portion. The nose mask is characterized in that plural products can be placed in a container to be carried while outside, so that the mask can be used by fitting to a nose anytime the need arises. In the nose mask of the present invention, the arrangement axle is inserted from nares into the nasal vestibule, and corresponding to various uses such as for swimming, filtering pollen, dust, and malodor in the air, and treating physical conditions, various mask portions are prepared for the user to selectively use in the nose mask.

The arrangement axle has the braces to sandwich the nasal septum when the arrangement axle is inserted from the nares into the nasal vestibule. The length of the arrangement axle to be inserted is approximately 15 mm from the nares to avoid causing the problem that the mask is easily released by the inner pressure of sneezing, as the arrangement axle is not directly contacting an inner surface of mucous membrane of the nasal cavity so as not to cause sneezing by stimulus.

The nose mask is able to prevent a nose from running out by means of a mask portion with hygroscopicity. Some of the masks have mask portions which liquid, selected from a group of remedies for pollinosis, nose drug for stopping nose bleeding, and a perfume for de-odorizing is provided in advance. The drug or the perfume can be positioned in the nares and evaporated and absorbed so as to work effectively. The liquid impregnated in the mask portion is heated and evaporated by body temperature, and absorbed into the nasal cavity when breathing. The nose mask is also used as a sanitary tool for effective medical treatment.

The present invention provides the nose mask, which can be used in different cases including a case of going to a place with polluted air, a case of medical treatment, and a case where swimming is performed, without spoiling the appearance of a nose.

The invention claimed is:

1. A nose mask comprising:

an arrangement axle;

a mask portion removably mounted on the arrangement axle, wherein the arrangement axle can be inserted from nares into a nasal vestibule to attach the mask portion to a nasal cavity of a user, the mask portion including a cellulose sponge and a pair of round-shaped filters arranged on opposite sides of the cellulose sponge, the round-shaped filters being capable of filtering polluted air and collecting dust, and the cellulose sponge being capable of absorbing and buffering liquid; and a cap and a stopper securing the mask portion to a portion of the arrangement axle by sandwiching the mask portion between the cap and the stopper, wherein the first and second round shaped filters have a diameter that is larger than a maximum outer diameter of the cellulose sponge, and wherein the cap includes structure defining a central passage receiving the arrangement axle, and a first engagement portion engaging an engagement member of the arrangement axle to secure the cap on the arrangement axle, and a second engagement portion engaging an engagement member of the stopper in order to sandwich the filters and the cellulose sponge between the cap and the stopper thereby preventing the mask portion from being disengaged from the arrangement axle by a force applied transversely to a plane direction of the filters.

2. The nose mask as claimed in claim 1, wherein the structure defining the central passage extends through the round shaped filters and the cellulose sponge.

3. The nose mask as claimed in claim 1, wherein the first and second round shaped filters are positioned to contact internal surfaces of a nasal vestibule when the mask portion is inserted therein.

4. A nose mask comprising:

an axle;

a first mask portion removably mounted on a first end portion of the axle;

a second mask portion removably mounted on a second end portion of the axle, wherein the first and second end portions of the axle can be inserted from nares into a nasal vestibule to attach the first and second mask portions to a nasal cavity of a user, each of the mask portions includes a cellulose sponge and a pair of disk-shaped filters arranged on opposite sides of the cellulose sponge, the filters being capable of filtering polluted air, and the cellulose sponge being capable of absorbing liquid; and a first cap and a first stopper securing the first mask portion to the first end portion of the by sandwiching the mask portion between the first cap and the first stopper, wherein each of the first and second disk-shaped filters has a diameter that is larger than a maximum outer diameter of the respective cellulose sponge, and wherein the first cap includes structure defining a central passage receiving the first end portion of the axle, a first engagement portion engaging an engagement member of the axle to secure the first cap on the first end portion of the axle, and a second engagement portion engaging an engagement member of the first stopper in order to sandwich the corresponding filters and the cellulose sponge between the first cap and the first stopper thereby preventing the first mask portion from being disengaged from the axle by a force applied transversely to a plane direction of the filters.

5. The nose mask as claimed in claim 4, wherein the structure defining the central passage extends through the circular disk-shaped filters and the cellulose sponge.

6. The nose mask as claimed in claim 4, wherein the first and second disk-shaped filters are positioned to contact internal surfaces of a nasal vestibule when the mask portion is inserted therein.

7. The nose mask as claimed in claim 4, wherein each of the first and second disk-shaped filters comprises a circular disk.

* * * * *